US011191835B2

(12) United States Patent
Isaac-Lam

(10) Patent No.: US 11,191,835 B2
(45) Date of Patent: Dec. 7, 2021

(54) CHLORIN-VITAMIN CONJUGATES

(71) Applicant: Purdue Research Foundation, West Lafayette, IN (US)

(72) Inventor: Meden Fruel Isaac-Lam, Michigan City, IN (US)

(73) Assignee: Purdue Research Foundation, West Lafayette, IN (US)

( * ) Notice: Subject to any disclaimer, the term of this patent is extended or adjusted under 35 U.S.C. 154(b) by 34 days.

(21) Appl. No.: 16/877,558

(22) Filed: May 19, 2020

(65) Prior Publication Data

US 2020/0276310 A1    Sep. 3, 2020

Related U.S. Application Data

(63) Continuation of application No. 16/220,057, filed on Dec. 14, 2018, now Pat. No. 10,806,788.

(60) Provisional application No. 62/620,520, filed on Jan. 23, 2018.

(51) Int. Cl.
| | | |
|---|---|---|
| *A61K 41/00* | (2020.01) | |
| *A61P 35/00* | (2006.01) | |
| *A61K 31/409* | (2006.01) | |
| *A61K 47/54* | (2017.01) | |
| *A61K 31/19* | (2006.01) | |
| *A61K 31/315* | (2006.01) | |
| *A61K 31/295* | (2006.01) | |
| *A61K 31/282* | (2006.01) | |
| *A61K 31/4188* | (2006.01) | |
| *A61K 47/55* | (2017.01) | |

(52) U.S. Cl.
CPC .......... *A61K 41/0071* (2013.01); *A61K 31/19* (2013.01); *A61K 31/282* (2013.01); *A61K 31/295* (2013.01); *A61K 31/315* (2013.01); *A61K 31/409* (2013.01); *A61K 31/4188* (2013.01); *A61K 47/546* (2017.08); *A61K 47/551* (2017.08); *A61P 35/00* (2018.01)

(58) Field of Classification Search
CPC .... A61K 31/19; A61K 31/282; A61K 31/295; A61K 31/315; A61K 31/409; A61K 31/4188; A61K 41/0071; A61K 47/546; A61K 47/551; A61P 35/00

USPC ........................................................ 514/359
See application file for complete search history.

(56) References Cited

U.S. PATENT DOCUMENTS

| | | | | |
|---|---|---|---|---|
| 6,090,788 A * | 7/2000 | Lurie | ..................... | A61K 31/00 514/23 |
| 8,454,991 B2 * | 6/2013 | Woo | .................... | A61K 41/0057 424/449 |
| 8,703,427 B2 * | 4/2014 | Deonarain | .............. | A61P 25/00 435/7.1 |
| 2006/0276339 A1 * | 12/2006 | Windsor | ................ | A01N 37/38 504/127 |
| 2007/0020241 A1 * | 1/2007 | Wilson | ............... | A61K 41/0071 424/93.6 |
| 2008/0193376 A1 * | 8/2008 | Tawakol | ................ | A61K 51/08 424/1.61 |
| 2009/0053247 A1 * | 2/2009 | Deonarain | ......... | A61K 49/0013 424/178.1 |
| 2009/0204057 A1 * | 8/2009 | Woo | .................... | A61K 41/0057 604/20 |
| 2011/0021974 A1 * | 1/2011 | Shantha | .................. | A61P 27/02 604/20 |
| 2012/0101033 A1 * | 4/2012 | Shantha | .................. | A61P 27/02 514/6.5 |

OTHER PUBLICATIONS

Nyuchev, Alexander V et al.(STN, 2017:1891156 HCAPLUS, DN:168:33090; Mendeleev Communications (2017), 27(6), 610-612 CODEN: MENCEX; ISSN: 0959-9436; Digital ID: 10.1016/j.mencom.2017.11.024, The iron complex of dimethyl chlorin e6-thioctic acid conjugate and its monolayers on the water and gold surfaces).*
Alexander Nyuchev et al. (STN-HCAPLUS, AN 2015:1385583;DN 163:659971;Synthesis, 2015), 47(23),3717-3726), CODEN: SYNTBF; ISSN: 1437-210X, Digital Object ID: 10.1055/s-0034-1378876; Journal;(online computer file; Models for Multifunctional Drug Development); Other Source(s): CASREACT 163:659971).*
Meden F. Isaac-Lam, etc., Biotinylated Chlorin and Its Zinc and Indium Complexes: Synthesis and In Vitro Biological Evaluation for Photodynamic Therapy, Pharmaceuticals (Basel). Jun. 2017; 10(2): 41.

* cited by examiner

*Primary Examiner* — Sabiha N Qazi
(74) *Attorney, Agent, or Firm* — Purdue Research Foundation

(57) ABSTRACT

The present disclosure relates to novel chlorin-vitamin conjugates and method of making and using the chlorin-vitamin conjugates.

6 Claims, No Drawings

CHLORIN-VITAMIN CONJUGATES

CROSS REFERENCE

The present U.S. patent application is related to and claims the priority benefit of U.S. Provisional Patent Application Ser. No. 62/620,520, filed Jan. 23, 2018, the contents of which is hereby incorporated by reference in its entirety.

TECHNICAL FIELD

The present disclosure relates to novel chlorin-vitamin conjugates and method of making and using the chlorin-vitamin conjugates.

BACKGROUND

This section introduces aspects that may help facilitate a better understanding of the disclosure. Accordingly, these statements are to be read in this light and are not to be understood as admissions about what is or is not prior art.

Photodynamic therapy (PDT) is a cancer treatment that involves delivery of a fluorophore known as photosensitizer (PS) to tumor tissues upon systemic administration and activation with visible light (600-800 nm) in the presence of endogenous oxygen. Excitation of PS with light in the red or near infrared (NIR) region generates cytotoxic reactive oxygen species (ROS), including singlet oxygen ($^1O_2$) to cause irreversible destruction of tumor cells, and to induce immune inflammatory responses and damage to tumor microvasculature. PDT is an FDA-approved treatment for bronchial, esophageal, gastric, cervical, skin, head, and neck cancers. However, PDT has certain limitations. Photosensitizer selectivity and efficacy which continue to be the major barrier for widespread acceptance of PDT in clinical practice must be improved to optimize anticancer treatment. Characteristics of ideal photosensitizers include low dark toxicity, high selectivity for tumors over normal tissues, high quantum yield of light-induced triplet state oxygen formation, and rapid clearance from the body. In PDT and in conventional cancer chemotherapy, increasing the amount of anticancer drugs is often necessary to achieve a linear response in killing cancer cells causing undesirable increase in toxicity to normal healthy cells due to non-selective tissue targeting.

Targeted therapy for cancer treatment exploiting ligands for selective delivery of pharmaceuticals to malignant cells is a strategy to improve anticancer drugs for treatment and imaging. Cancer cells overexpress tumor-specific receptors which can serve as targets to deliver photosensitizers into tumors. In particular, rapidly proliferating cancer cells require certain vitamins to sustain growth-causing vitamin receptors to be overexpressed on the cancer cell surface. B vitamins such as folic acid (B9), biotin (B7), riboflavin (B2), and cobalamin (B12) are essential vitamins for survival of all living cells, including the growth of cancerous cells. In contrast to folate receptors, which gained considerable attention as excellent biomarkers for targeted drug delivery, there are only few studies done on other B vitamin receptors.

There is still a need to develop novel photosensitizers for PDT that may provide low dark toxicity and high selectivity for tumors over normal tissues.

SUMMARY

One of the primary objectives of the present disclosure is to develop novel photosensitizers for PDT that may provide low dark toxicity and high selectivity for tumors over normal tissues.

In one embodiment, the present disclosure provides a chlorin-vitamin conjugated compound of formula I,

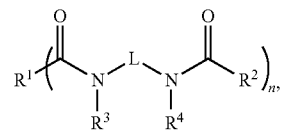

or a pharmaceutically acceptable salt, hydrate, metal complex thereof, wherein $R^1$ is a chlorin moiety;

$R^2$ is a vitamin moiety;

$R^3$ and $R^4$ are independently H or $C_1$-$C_4$ branched or straight alkyl;

L is a branched or straight $C_2$-$C_{12}$ linker, wherein at least one carbon of L is optionally substituted by an oxygen; and n is 1-3, wherein said chlorin is selected from the group consisting of:

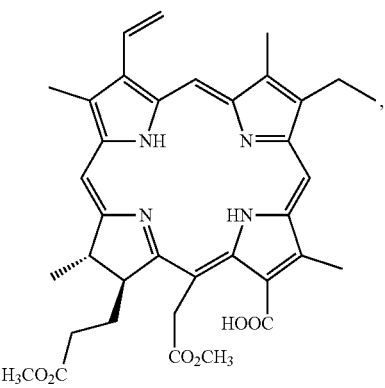

and

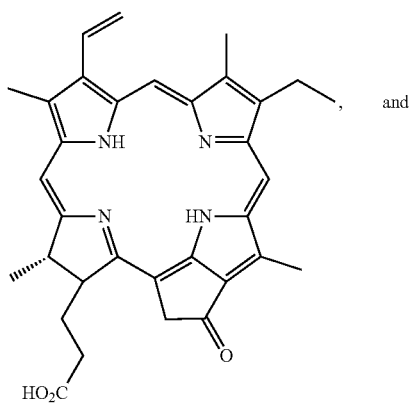

-continued

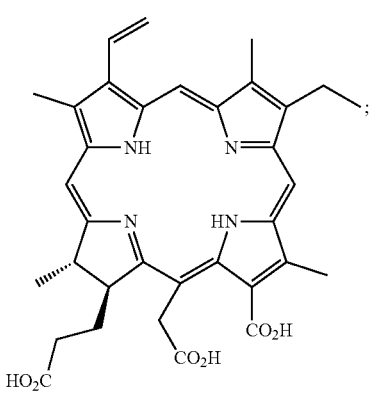

wherein said vitamin is selected from the group consisting of biotin, bexarotene, lipoic acid, pantothenic acid, desthiobiotin, and biocytin; and wherein said chlorin-vitamin conjugated compound is formed through at least one carboxylic acid group of said chlorin and one carboxylic acid group of said vitamin.

In one embodiment, the present disclosure provides a method of treating breast cancer comprising administering a pharmaceutical composition of the chlorin-vitamin conjugated compound of formula I.

DETAILED DESCRIPTION

For the purposes of promoting an understanding of the principles of the present disclosure, reference will now be made to the embodiments, and specific language will be used to describe the same. It will nevertheless be understood that no limitation of the scope of this disclosure is thereby intended.

In the present disclosure the term "about" can allow for a degree of variability in a value or range, for example, within 10%, within 5%, or within 1% of a stated value or of a stated limit of a range.

In the present disclosure the term "substantially" can allow for a degree of variability in a value or range, for example, within 90%, within 95%, or within 99% of a stated value or of a stated limit of a range.

In one embodiment, the present disclosure provides a chlorin-vitamin conjugated compound of formula I,

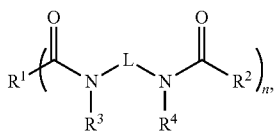

or a pharmaceutically acceptable salt, hydrate, metal complex thereof, wherein $R^1$ is a chlorin moiety;

$R^2$ is a vitamin moiety;

$R^3$ and $R^4$ are independently H or $C_1$-$C_4$ branched or straight alkyl;

L is a branched or straight $C_2$-$C_{12}$ linker, wherein at least one carbon of L is optionally substituted by an oxygen; and n is 1-3, wherein said chlorin is selected from the group consisting of:

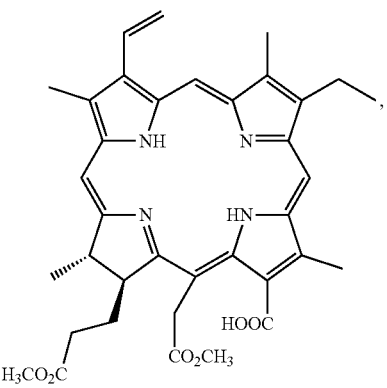

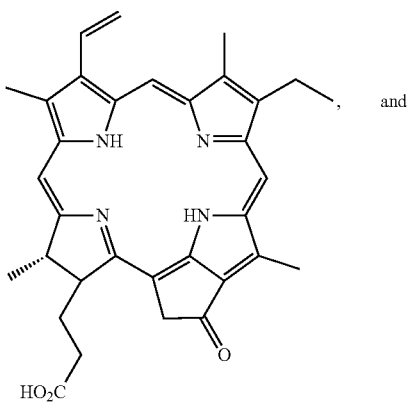

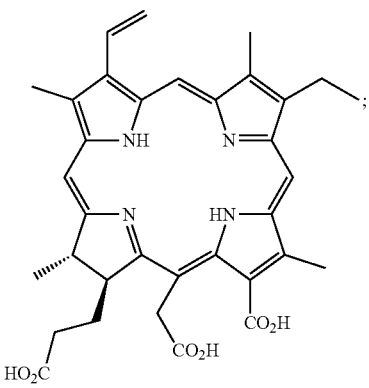

wherein said vitamin is selected from the group consisting of biotin, bexarotene, lipoic acid, pantothenic acid, desthiobiotin, and biocytin; and wherein said chlorin-vitamin conjugated compound is formed through at least one carboxylic acid group of said chlorin and one carboxylic acid group of said vitamin.

In one preferred embodiment, the chlorin is:

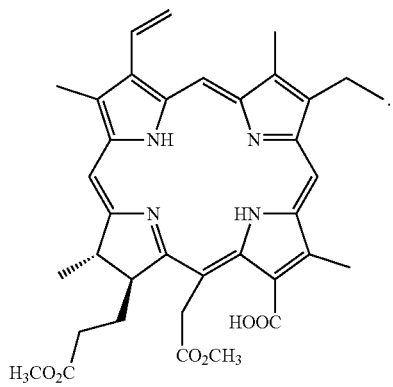 [SMILES: C=Cc1c(C)c2cc3nc(c(CC(=O)OC)c4[nH]c(cc5nc(cc1[nH]2)C(C)=C5CC)c(C)c4C(=O)O)[C@@H](CCC(=O)OC)[C@@H]3C]

In one preferred embodiment, the linker L of formula I is a straight $C_6$ linker.

In one preferred embodiment, when a compound of formula I is a metal complex formed by a chlorin moiety and a metal ion, the metal is selected from the group consisting of zinc (Zn), indium (In), palladium (Pd) and platinum (Pt).

In one preferred embodiment, the vitamin is biotin or bexarotene.

In one preferred embodiment, the vitamin is bexarotene.

In one embodiment, the chlorin-vitamin conjugated compound is selected from a group consisting of:

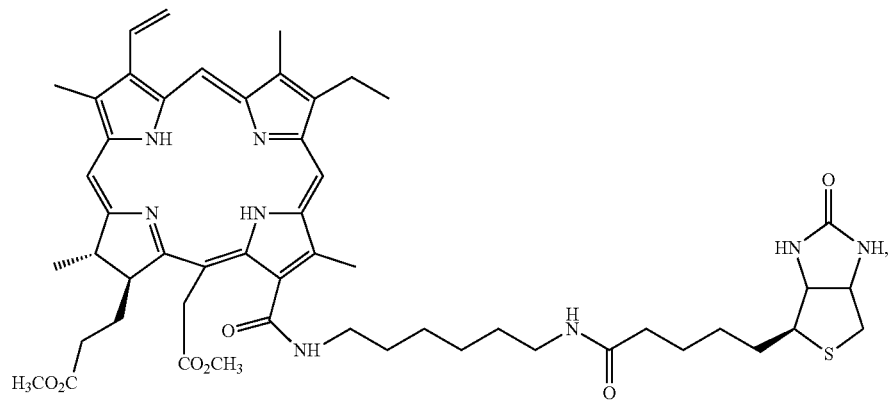

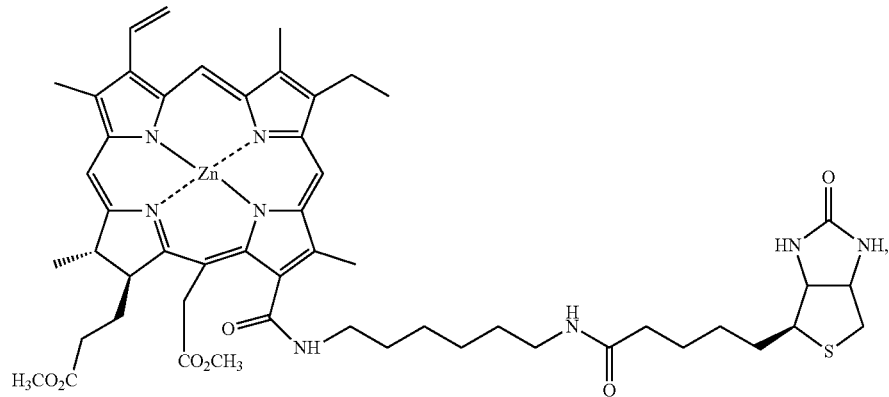

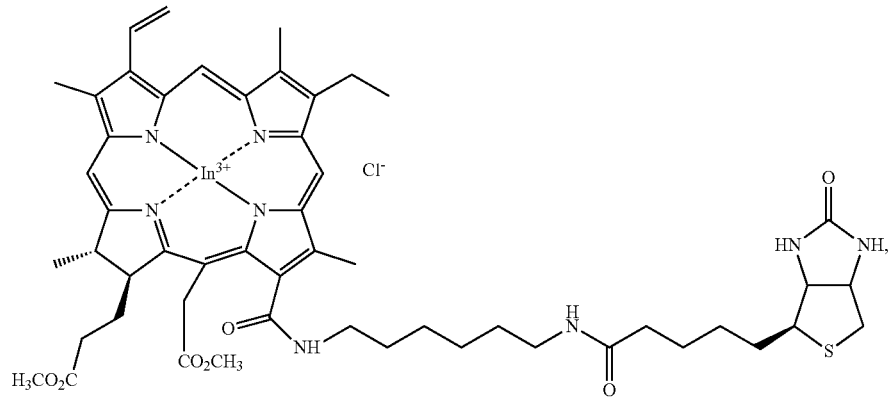

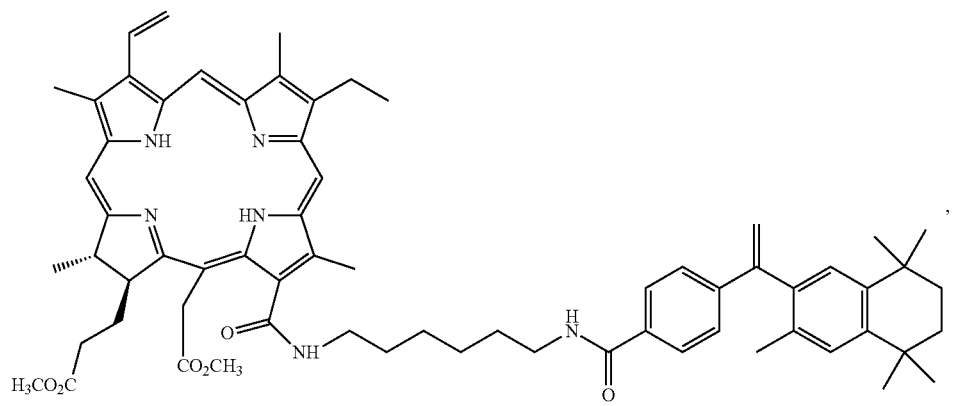

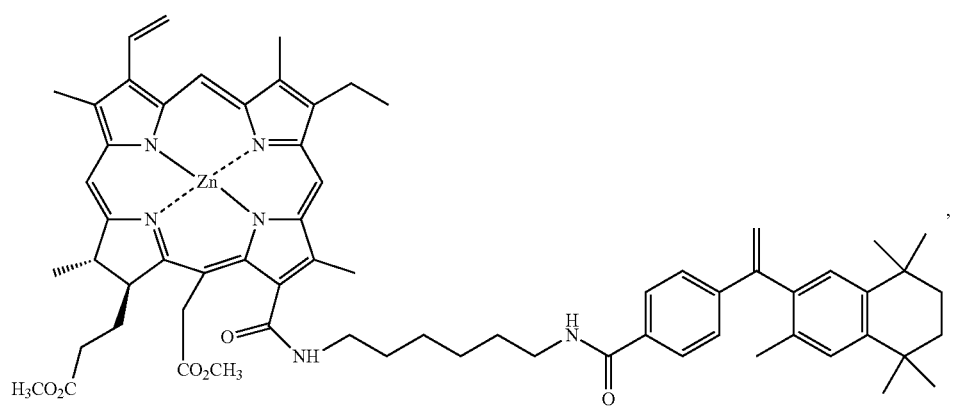

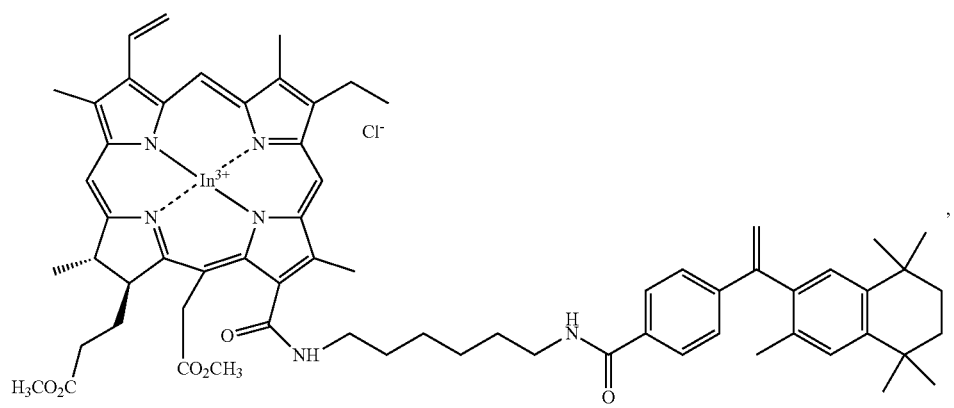

and a pharmaceutically acceptable salt or hydrate thereof.

In one embodiment, the present disclosure provides a method of treating a disease responsive to the chlorin-vitamin conjugated compound of formula I. In one aspect, the disease is a cancer, wherein the cancer may be but is not limited to head and neck cancer, breast cancer, prostate cancer, lung cancer, liver cancer, gynecological cancer, cervical cancer, brain cancer, melanoma, colorectal cancer bladder cancer, ovarian cancer, or gastrointestinal cancer. In one aspect, the cancer is breast cancer. Examples of breast cancer include, but are not limited to triple-negative breast cancer (TNBC) or triple-positive breast cancer TPBC). In one aspect, the breast cancer is triple-negative breast cancer (TNBC).

In one embodiment, the present disclosure provides that the chlorin-vitamin conjugated compound of claim 1 is used as a photosensitizers for photodynamic therapy (PDT).

In one embodiment, the present disclosure provides that the use of the chlorin-vitamin conjugate composition of the present disclosure in the manufacture of a medicament for the treatment of any cancer as disclosed in the disclosure.

The present disclosure provides pharmaceutical compositions comprising a chlorin-vitamin conjugate composition of the present disclosure, and one or more pharmaceutically acceptable carriers, diluents or excipients. Further, the present disclosure provides a method of treating a cancer as disclosed comprising administering to a patient in need thereof a pharmaceutical composition of the present disclosure.

Chemistry

Bexarotene was purchased from ChemLeader Biomedical Co. Ltd. (Shanghai, China). All solvents and reagents were purchased mainly from Sigma Aldrich Chemical Co. (St. Louis Mo., USA). All air and moisture sensitive reactions were performed in anhydrous solvents under nitrogen atmosphere. Chromatographic purifications were performed in normal phase preparative TLC (thin-layer chromatography) plate (Analtech). Reactions were monitored using polyester backed normal phase analytical TLC plate (Merck, Silica gel 60 $F_{254}$ precoated 200 μm) and detected with UV light (λ=254 nm). NMR spectra were acquired with a Bruker Avance NMR spectrometer (400 MHz for $^1$H, 100 MHz for $^{13}$C). Chemical shifts are reported in δ ppm referenced according to the deuterated solvents used as internal standards: $CDCl_3$ 7.24 ppm ($^1$H), 77.23 ppm ($^{13}$C). High resolution mass spectra were obtained on a Bruker micrOTOF-II ESI mass spectrometer. All compounds synthesized were isolated and purified in >95% purity as confirmed by $^1$H, $^{13}$C, 2D COSY (Correlated Spectroscopy), DEPT 135 (Distortion-less Enhancement by Polarization Transfer), HSQC (Heteronuclear Single Quantum Correlation) NMR spectra. Sample purity was also checked using ThermoScientific Ultimate 3000 HPLC (high performance liquid chromatography) equipped with a diode-array four-channel variable UV-visible detector, an autosampler and a fraction collector using a reverse-phase column (C-18, 4.6×50 mm, 3.5 μm) in isocratic mobile phase (100% acetonitrile) visualizing at λ=405 and 665 nm with a flow rate of 1 mL/min.

Preparation 1: $13^1$-Hexamethylenediaminylchlorin $e_6$ dimethyl ester

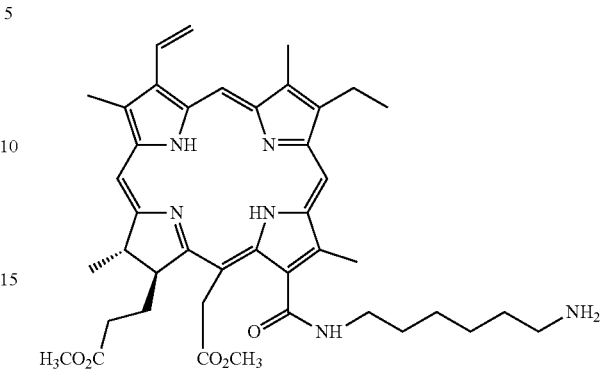

Methyl pheophorbide a (100 mg, 0.165 mmol) was dissolved in dry $CH_2Cl_2$ and stirred under nitrogen for 10 min. Then N-t-butyloxycarbonyl-1,6-hexanediamine or (200 mg, 0.93 mmol) dissolved in 1 mL $CHCl_3$ (dried over molecular sieves) was added in to the solution and the mixture was stirred for 24 h. The reaction was monitored by TLC (10% acetone/$CH_2Cl_2$) until reaction showed disappearance of the starting material methyl pheophorbide a. Additional amine may be added to complete the reaction. Solvent was evaporated and the residue was purified by preparative TLC plate using 8% acetone/$CH_2Cl_2$ to afford 130 mg (0.158 mmol, 96% yield) of $13^1$-hexamethylenediaminyl(Boc) chlorin $e_6$ dimethyl ester. The $13^1$-hexamethylenediaminyl (Boc) chlorin $e_6$ dimethyl ester (65 mg, 0.085 mmol) was dissolved in dry $CH_2Cl_2$ (4 mL) under nitrogen. Reaction mixture was cooled in an ice bath, and TFA (1.2 mL) was added. Nitrogen was removed and the solution was stirred for 3 h. Complete deprotection of Boc group was monitored by TLC (10% acetone in $CH_2Cl_2$), and then the solution was washed twice with saturated aqueous $NaHCO_3$ solution. After drying over anhydrous $Na_2SO_4$, solvent was removed to yield 50 mg (0.075 mmol, 88% yield) of Preparation 1. HRMS (MALDI-TOF) m/z 723.4214 [M]$^+$; calcd for $C_{42}H_{54}N_6O_5$ 723.4228.

Example 1: $13^1$-Hexamethylenediaminyl-biotinyl-chlorin $e_6$ dimethyl ester

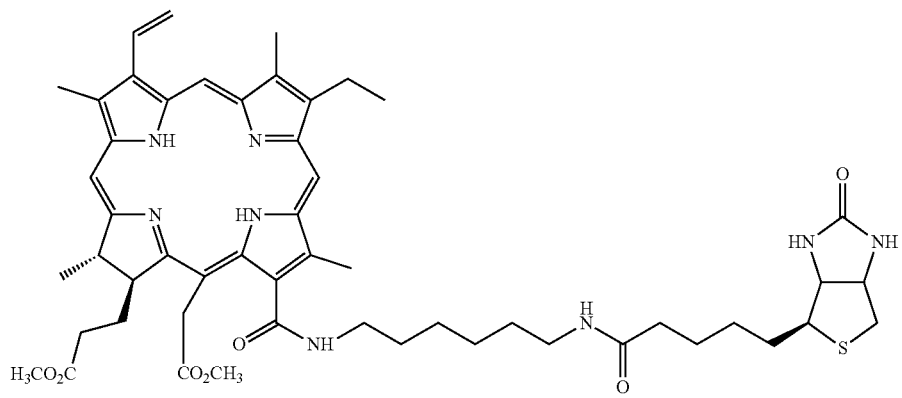 [SMILES: C=Cc1c(C)c2cc3nc(c(CC(=O)OC)c4[nH]c(cc5nc(cc1[nH]2)C(C)=C5CC)c(C)c4C(=O)NCCCCCCNC(=O)CCCC[C@@H]1SCC2NC(=O)NC21)[C@@H](CCC(=O)OC)[C@@H]3C]

In a dry round bottom flask containing Preparation 1 (92 mg, 0.128 mmol), biotin (48 mg, 0.138 mmol), 4-(4,6-dimethoxy-1,3,5-triazin-2-yl)-4-methylmorpholinium chloride (DMTMM, 42 mg, 0.150 mmol) was stirred in dry $CH_2Cl_2$ (25 mL) under nitrogen overnight for 12 h. The reaction was monitored by TLC (10% methanol in $CH_2Cl_2$) until reaction showed disappearance of the starting amine. Solvent was evaporated and the residue was purified by preparative TLC plate using the same solvent system to afford 76 mg (0.072 mmol, 57% yield) of Example 1. HRMS (MALDI-TOF) m/z 949.6150 [$M^+$], calcd for $C_{52}H_{68}N_8O_7S$ 949.2311.

Example 2: $13^1$-Hexamethylenediaminyl-bexarotenylchlorin $e_6$ dimethyl ester

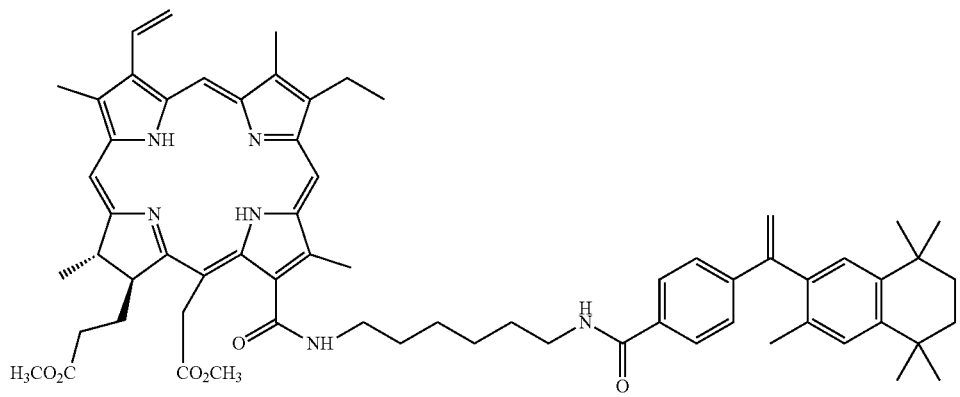 [SMILES: C=Cc1c(C)c2cc3nc(c(CC(=O)OC)c4[nH]c(cc5nc(cc1[nH]2)C(C)=C5CC)c(C)c4C(=O)NCCCCCCNC(=O)c1ccc(C(=C)c2cc4c(cc2C)C(C)(C)CCC4(C)C)cc1)[C@@H](CCC(=O)OC)[C@@H]3C]

Example 2 was prepared with similar method of preparing Example 1. HRMS (ESI) m/z 1053.6256 [$M$]$^+$, calcd for $C_{66}H_{80}N_6O_6$ 1053.6212.

Example 3: Zn(II)-$13^1$-Hexamethylenediaminyl-Biotinylchlorin $e_6$ dimethyl ester

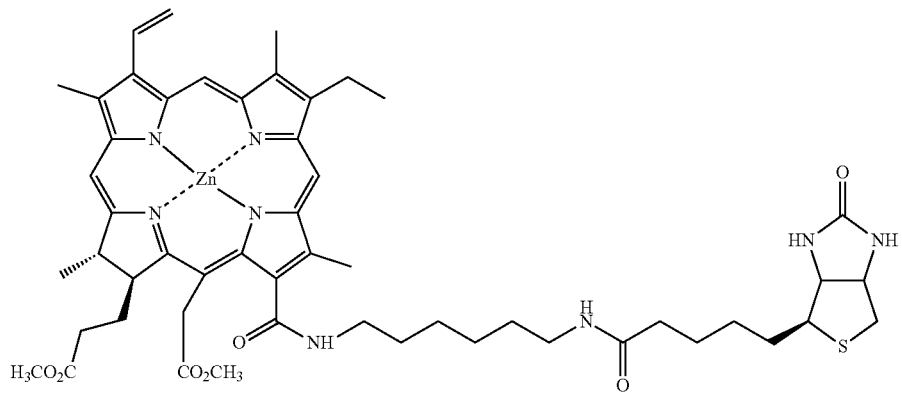

In a dry round bottom flask, Example 1 (50 mg, 0.053 mmol) was dissolved in 5 mL methanol. Saturated methanolic solution of zinc(II) acetate (5 mL) were added to the mixture and stirred for 2 h. After checking spectrophotometrically for completion, the reaction mixture was washed with saturated aqueous solution of sodium bicarbonate, followed by washing with water (3×50 mL), and extracted with dichloromethane. The organic layer was dried over anhydrous sodium sulfate and the organic solvent was evaporated under high vacuum. The crude product was purified by preparative TLC plate using 3% methanol-dichloromethane to afford 40 mg (0.039 mmol, 73% yield) of the title compound. HRMS (MALDI-TOF) m/z 1033.3986 [M$^+$+Na], calcd for $C_{52}H_{66}N_8NaO_7SZn$ 1033.3959.

Example 4: Zn(II)-13$^1$-Hexamethylenediaminyl-bexarotenylchlorin e$_6$ dimethyl ester

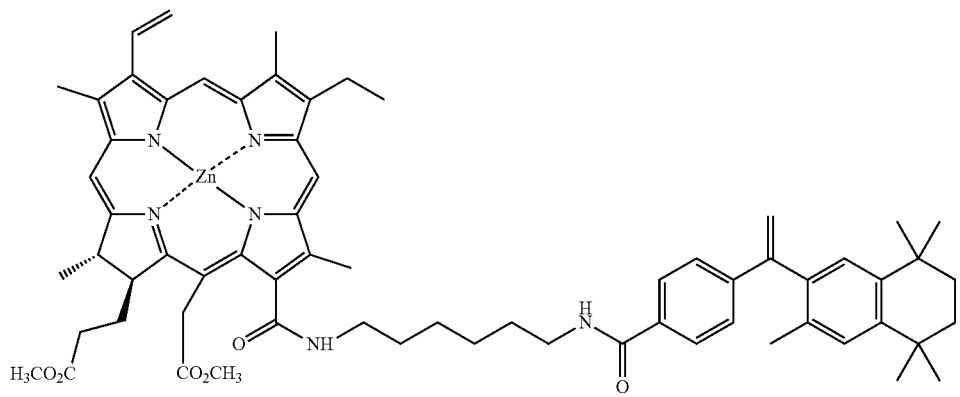

Example 4 was prepared from Example 2 with similar method of preparing Example 3. HRMS (ESI) m/z 1115.5365 [M$^+$+H], calcd for $C_{66}H_{79}N_6O_6Zn$ 1115.5347.

Example 5: 13$^1$-Hexamethylenediaminyl-Biotinyl-chlorin e$_6$ dimethyl ester indium (III) chloride

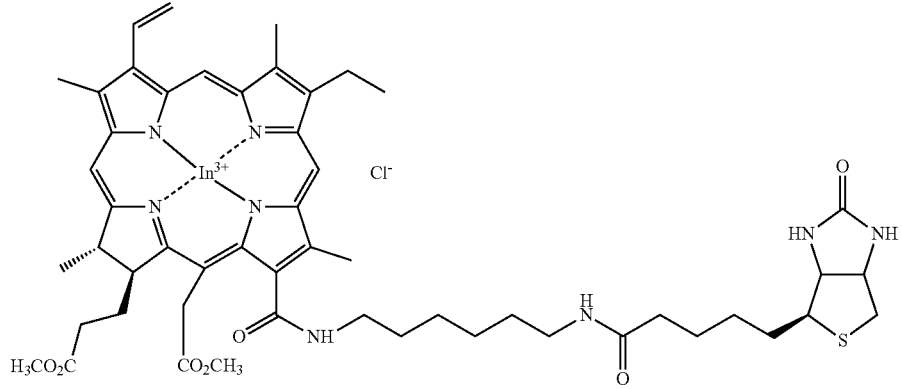

In a dry round bottom flask, Example 1 (50 mg, 0.053 mmol) was dissolved in 15 mL toluene, then sodium acetate (500 mg), anhydrous potassium carbonate (500 mg) and indium chloride (300 mg) were added. The reaction mixture was refluxed under nitrogen atmosphere overnight. After checking spectrophotometrically for complete metal insertion, the reaction mixture was neutralized with acetic acid and washed with water (3×50 mL), then the organic layer was dried over anhydrous sodium sulfate. Solvent was evaporated under high vacuum. The crude product was purified by preparative TLC plate using 3% methanol-dichloromethane to afford 45 mg (0.041 mmol, 77% yield) of the title compound.

Example 6: 13$^1$-Hexamethylenediaminyl-bexarotenylchlorin e$_6$ dimethyl ester indium (III) chloride

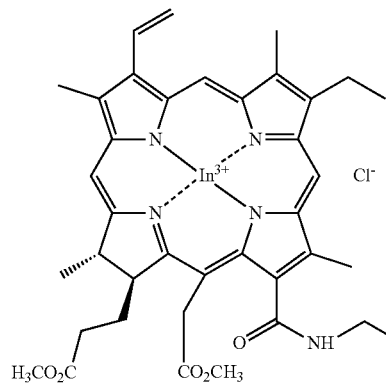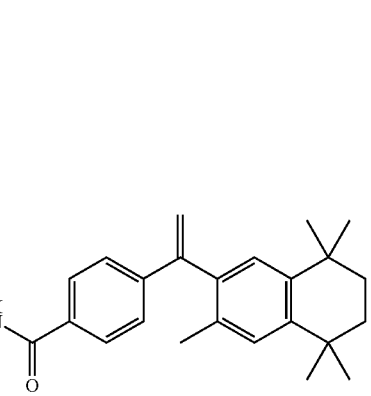

In a dry round bottom flask, Example 2 (20 mg, 0.019 mmol), sodium acetate (170 mg), and indium chloride (100 mg) were added, and dissolved in acetic acid (3 mL). The reaction mixture was refluxed under nitrogen atmosphere overnight. After checking spectrophotometrically for complete metal insertion, the reaction mixture was neutralized with saturated NaHCO$_3$, and extracted with dichloromethane (20 mL). The organic layer was washed with water, then dried over anhydrous sodium sulfate. Solvent was evaporated under high vacuum. The crude product was purified by preparative TLC plate using 4% methanol-dichloromethane to afford 13 mg (0.011 mmol, 57% yield) of the title compound. HRMS (ESI) m/z 1165.5026 [M$^+$–Cl], calcd for C$_{66}$H$_{78}$ClInN$_6$O$_6$ 1201.4783.

Assays

In Vitro Cytotoxicity Assay

Mouse colon carcinoma cell line CT26. WT was purchased from the American Type Culture Collection (ATCC CRL-2638). CT26 cells were cultured in RPMI 1640 medium (ATCC) and were grown to 80%-90% confluence in 75-cm$^2$ culture flasks (Corning, Corning, N.Y., USA) for about a week (5-6 days) in a humidified incubator (Fisher Scientific Isotemp, Waltham, Mass., USA) with 5% CO$_2$ at 37° C. During the incubation period, growth media was changed once with fresh pre-warmed medium (pH 7.2). To harvest the cells, old growth media was aspirated and 5 mL 0.25% trypsin solution (Thermo Sci Hyclone, Waltham, Mass., USA) were added. The cells were incubated for 10 min and gently scraped to detach cells from the flask walls. Clumped cells were broken up gently and 1 mL of the trypsinized cell homogenate suspension was transferred into a new T75 cell culture flask containing pre-warmed media (20 mL) for further culturing.

Human mammary epithelial carcinoma cell lines purchased from the American Type Culture Collection ZR-75-1 (ATCC CRL-1500) and BT-549 (ATCC HTB-122) were cultured according to ATCC protocol. Briefly, ZR-75-1 cells were grown in RPMI 1640 medium (ATCC), while BT-549 were grown in RPMI 1640 containing 0.023 IU/mL insulin. Both were supplemented with 10% fetal bovine serum (FBS). Cells were grown to 80-90% confluence in 75-cm$^2$ culture flasks (Corning) for 4-5 days in a humidified incubator (Fisher Scientific Isotemp) with 5% CO$_2$ at 37° C. During the incubation period, growth media was changed once with fresh pre-warmed media (pH 7.2). To harvest the cells, old growth media was aspirated out and 3 mL 0.25% trypsin solution (Thermo Sci Hyclone) were added. The cells were incubated for 5 min and the cell pellet after centrifugation was resuspended in 3 mL media, broken up gently, then 1 ml of suspended cells was transferred into a new T75 cell culture flask containing pre-warmed media (20 mL) for further culturing.

Cell Survival Assay

Cells were grown to confluence in a 96-well plate (5×10$^4$ cells/well) and treated for 24 h with compounds or photosensitizers of varying concentrations ranging from 5 nM to 50 µM) in growth media from a stock solution of 10 mM in DMSO (dimethyl sulfoxide, Fisher). After 24 h treatment, old growth media containing the PS or compounds were aspirated out and replaced with fresh media. Plates were then positioned below a non-coherent LumaCare LC-122 650 nm light source for 1, 2, and 5 min at an energy fluence rate of 16 mW/cm$^2$ (measured using a Newport optical power meter Model 840). Unirradiated cells served as control samples. The following day, cells were washed with pre-warmed PBS, and MTT (3-[4,5-dimethyl-thiazol-2-yl]-2,5-diphenyltetrazolium bromide, Sigma, 0.3 mg/mL) in PBS was added to each well. Samples were allowed to incubate for additional 2 h, after which dark blue crystals formed. DMSO was added to each well and plates were shaken at room temperature for 1 h to dissolve the purplish-blue formazan crystals. Absorbance values at 490 nm were measured on a microplate reader (BioRad 550). Cell survival was calculated based on the absorbance of the untreated cells alone (as control) and were directly proportional to the number of viable cells in culture. Results were reported as average of triplicate measurements.

Results from cell viability assay indicated that biotin is not toxic to the colon cancer cells in the dark and in the presence of light for concentration of up to 50 μM, which is the maximum concentration used for the assay. Compared to the starting methyl pheophorbide (MePheo) which serves as the control, Example 1 increased cell inhibition upon irradiation by approximately 19%. The indium complex, Example 5, compared to either the starting MePheo, the unmetallated Example 1, or the zinc complex ZnCBTN, Example 3, caused a marked decrease in cell proliferation of colon cancer cells by 30% and 40%-50% upon irradiation for 2 and 5 min, respectively.

The dark toxicity of the synthesized photosensitizer linked to biotin (Example 1) or bexarotene (Example 2) compared to the starting methyl pheophorbide a (MePheo) after 24-hr treatment of triple-negative breast cancer cells were evaluated. Example 1 has a dose response in the absence of light when TNBC cells were treated with as low as 5 μM showing an 86% cell survival, while no significant dark response was observed upon treatment with Example 2, Example 4 and MePheo. Example 3, Example 5 and Example 6 also exhibited dark toxicity. The dark toxicity of the synthesized photosensitizers to TNBC was ranked as follows: Example 3 (most phototoxic in the dark)>Example 1>Example 6>Example 5.

For TPBC cells, Example 3 is the most phototoxic in the dark compared to the other photosensitizers, and can be ranked according to the following: Example 3>Example 5>MePheo>Example 6, and the rest (Example 1, Example 2 and Example 4) showing no toxicity in unirradiated TPBC cells. No dark toxicity was observed for all the photosensitizers tested at ≤0.5 μM concentration in TNBC and TPBC cells.

Phototoxicity of Triple-Negative Breast Cancer Cell Line at Nanomolar Concentrations.

At a low concentration of 100 nM, only Example 1 showed a light-activation dose response when compared to Example 2 and MePheo in TNBC cells with a 60% cell inhibition at 5 min light dose (4.8 J cm$^{-2}$). However, doubling the concentration to 200 nM, Example 1 is still more effective than both Example 2 and MePheo in controlling TNBC cell growth with almost 50% reduction in cell proliferation at the lowest light dose used. All the other photosensitizers were ineffective for TNBC at this nanomolar concentration range. TPBC were totally unaffected by the other PSs at this low concentrations. Results indicated that Example 1 is a better photosensitizer than any of the PSs utilized in this investigation to inhibit the proliferation of the TNBC cell line.

Fluorescence Microscopy

Fluorescence microscopy was used to visualize and examine the cell morphological features before and after photosensitization. Specific cellular characteristics can identify the mechanism of cell death which can be exploited to understand therapeutic outcome.

Cells (1 mL aliquots) obtained from a diluted cell suspension were seeded into each well (1.7 cm$^2$, 5×10$^3$ cells/well) of a 4-well culture slide (BD Biosciences) and grown to confluence in 5% $CO_2$ at 37° C. for 3-4 days for attachment to the substratum. After aspirating the old growth media, 1 mL of the compound or photosensitizer (with varying concentrations) in fresh pre-warmed media at 37° C. was added to each well. After compound treatment for 24 h, cells were washed twice with 1 mL fresh growth media, and then irradiated with light using LumaCare LC-122 as described above. Cells were stained in the dark with Hoechst 33258 (Molecular Probes) in pre-warmed media for 10 min at 37° C., washed twice with filtered PBS, then fixed with filtered paraformaldehyde for 15 min in the incubator. After thorough liquid aspiration, the wells were removed and allowed to air dry in the dark for 1 h. Slides were protected with coverslips, whose edges were sealed using a clear fast-drying nail polish and allowed to dry at room temperature in the dark for 30 min. Images were recorded using fluorescence microscopy (DAPI for Hoechst 350-390 nm excitation and 460-490 nm emission filters) using an upright fluorescence microscope with Retiga imaging 2000R (Nikon Optiphot-2, 20× and 40×) and an image processing Nikon NIS-Elements V4.0 Qimaging software.

TABLE 1

Summary of cell survival (%) assay and cell morphological features based on fluorescence microscopy images after 24 h compound treatment followed by 2 min light irradiation (1.92 J cm$^{-2}$) on triple-negative BT549 and triple-positive ZR-75-1 breast cancer cell lines.

| Compounds | Triple-negative breast cancer cell BT549 | | Triple-positive breast cancer cell ZR-75-1 | |
|---|---|---|---|---|
| | % Cell Survival | Morphological Features | % Cell Survival | Morphological Features |
| Example 1 | 8.1 | Chromatin condensation, nuclear fragmentation | 4.2 | Chromatin condensation, nuclear fragmentation |
| Example 3 | 16 | Cell and nuclear shrinkage, reduced cell density | 15.4 | Cell and nuclear shrinkage, reduced cell density |
| Example 5 | 56 | Chromatin condensation, nuclear fragmentation | 12.9 | Cell debris apparent |
| Example 2 | 7.7 | Chromatin condensation, nuclear fragmentation | 4.6 | Cell and nuclear shrinkage, reduced cell density |
| Example 4 | 108 | Dispersed cells, intact nuclei, well-defined cytoplasm | 105 | Clustered cells, intact nuclei |
| Example 6 | 33 | Cell and nuclear shrinkage, reduced cell density | 80 | Clustered cells, intact nuclei |

TABLE 1-continued

Summary of cell survival (%) assay and cell morphological features based on fluorescence microscopy images after 24 h compound treatment followed by 2 min light irradiation (1.92 J cm$^{-2}$) on triple-negative BT549 and triple-positive ZR-75-1 breast cancer cell lines.

| Compounds | Triple-negative breast cancer cell BT549 | | Triple-positive breast cancer cell ZR-75-1 | |
|---|---|---|---|---|
| | % Cell Survival | Morphological Features | % Cell Survival | Morphological Features |
| Methyl pheophorbide a (control) | 21 | Chromatin condensation, nuclear fragmentation | 3.4 | Cell and nuclear shrinkage, reduced cell density |
| Bexarotene (control) | 111 | Dispersed cells, intact nuclei, well-defined cytoplasm | 110 | Clustered cells, intact nuclei, well-defined cytoplasm |
| Biotine (control) | 116 | Dispersed cells, intact nuclei, well-defined cytoplasm | 99 | Clustered clumped cells, intact nuclei, well-defined cytoplasm |

The novel chlorin-vitamin conjugates disclosed in the present disclosure can be promising photosensitizers for potential application in triple-negative breast cancer. One preferred compound such as Example 2 may be especially useful due to its relatively nonexistent dark cytotoxicity. The chlorin-biotin conjugate Example 1, which exhibited in vitro dark cytotoxicity at 5 µM concentration, can be useful for TNBC with proper adjustment of light dosage since Example 1 showed considerable potency at the nanomolar concentration range. Additionally, novel chlorin-vitamin conjugates can have applications for triple-positive breast cancer (ER$^+$/PR$^+$/HER2$^+$) by targeting the biotin receptors upregulated in cancer cell surface or the nuclear receptors, respectively, since comparatively no dark toxicity was observed at the highest concentration of Example 1 and Example 2 used in this study.

Those skilled in the art will recognize that numerous modifications can be made to the specific implementations described above. The implementations should not be limited to the particular limitations described. Other implementations may be possible.

The invention claimed is:

1. A chlorin-vitamin conjugated compound of formula I,

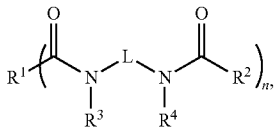

or a pharmaceutically acceptable salt, hydrate, metal complex thereof,
wherein
R$^1$ is a chlorin;
R$^2$ is a vitamin;
R$^3$ and R$^4$ are independently H or C$_1$-C$_4$ branched or straight alkyl;

L is a branched or straight C$_2$-C$_{12}$ linker, wherein at least one carbon of said C$_2$-C$_{12}$ linker is optionally substituted by an oxygen; and n is 1-3, wherein said chlorin is selected from the group consisting of:

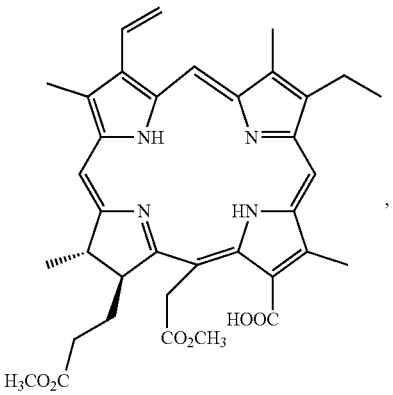

,

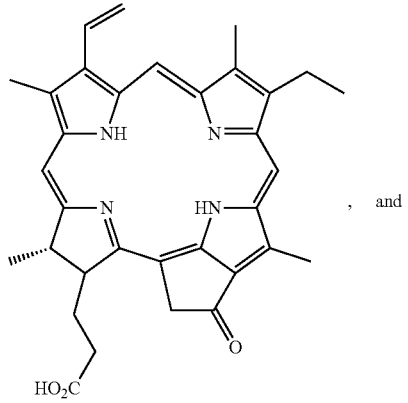

, and

-continued

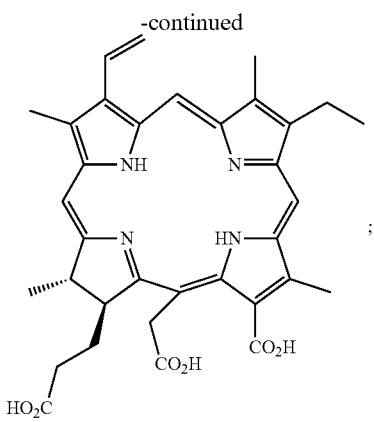

;

wherein said vitamin is selected from the group consisting of biotin, bexarotene, lipoic acid, pantothenic acid, desthiobiotin, and biocytin; and wherein said chlorin-vitamin conjugated compound is formed through at least one carboxylic acid group of said chlorin and one carboxylic acid group of said vitamin, wherein said metal complex is a metal complex of a metal selected from the group consisting of zinc (Zn), indium (In), palladium (Pd) and platinum (Pt).

2. The chlorin-vitamin conjugated compound of claim 1, wherein L is a straight $C_6$ linker.

3. A method of treating breast cancer comprising administering a pharmaceutical composition comprising the compound of claim 1.

4. The method of claim 3, wherein the breast cancer is triple-negative breast cancer or triple-positive breast cancer.

5. The method of claim 4, wherein the breast cancer is triple-negative breast cancer.

6. The method of claim 3, wherein the compound of claim 1 is used as a photosensitizer in photodynamic therapy (PDT).

* * * * *